United States Patent [19]
Schmid

[11] Patent Number: 5,271,087
[45] Date of Patent: Dec. 14, 1993

[54] DENTAL HANDPIECE FOR HEATING MEDIA UTILIZING A PTC RESISTOR AND SINTERED METAL COMPONENTS

[75] Inventor: Gerhard Schmid, Mittelberach, Fed. Rep. of Germany

[73] Assignee: Kaltenbach & Voight GmbH & Co.

[21] Appl. No.: 918,637

[22] Filed: Jul. 21, 1992

[30] Foreign Application Priority Data

Jul. 23, 1991 [DE] Fed. Rep. of Germany ....... 4124412

[51] Int. Cl.⁵ .................. A61C 17/02; F24H 1/12; H05B 3/12; H05B 1/02
[52] U.S. Cl. .................... 392/485; 165/907; 219/530; 219/540; 222/146.5; 239/133; 239/135; 392/383; 392/397; 392/474; 392/488; 392/497; 392/502; 433/32
[58] Field of Search .............. 392/480–485, 392/397, 379–385, 495, 473–477, 502; 433/32; 219/505, 530, 540; 165/907; 239/133, 135; 222/146.1, 146.5

[56] References Cited

U.S. PATENT DOCUMENTS

| Re. 31,841 | 3/1985 | Madsen et al. ........... 392/397 X |
| 1,277,621 | 9/1918 | Macklind ................. 392/495 |
| 2,187,470 | 1/1940 | Collins .................. 165/907 |
| 2,390,710 | 12/1945 | Henschel . |
| 3,334,400 | 8/1967 | Jaeger ................... 392/485 |
| 3,339,260 | 9/1967 | Burne et al. ............. 392/480 X |
| 3,476,293 | 11/1969 | Marcoux ................. 392/475 X |
| 4,088,269 | 5/1978 | Schlick ................. 219/505 |
| 4,371,777 | 2/1983 | Roller et al. ........... 392/480 |
| 4,414,052 | 11/1983 | Habata et al. .......... 219/505 X |
| 4,447,706 | 5/1984 | Eder et al. .............. 392/473 |
| 4,886,452 | 12/1989 | Löhn .................... 433/32 |
| 5,076,469 | 12/1991 | Pleuse et al. ............ 165/907 |

FOREIGN PATENT DOCUMENTS

| 282085 | 9/1988 | European Pat. Off. ........... 392/379 |
| 2252330 | 4/1974 | Fed. Rep. of Germany . |
| 2322191 | 11/1974 | Fed. Rep. of Germany . |
| 2804749 | 8/1979 | Fed. Rep. of Germany ...... 392/480 |
| 2920009 | 11/1980 | Fed. Rep. of Germany ........ 433/32 |
| 3734864 | 4/1989 | Fed. Rep. of Germany . |
| 3810051 | 10/1989 | Fed. Rep. of Germany ...... 392/480 |
| 1269231 | 7/1961 | France . |
| 1448217 | 9/1976 | United Kingdom . |

Primary Examiner—Anthony Bartis
Attorney, Agent, or Firm—Marshall, O'Toole, Gerstein, Murray & Borun

[57] ABSTRACT

A device for heating flowing media in a handpiece, particularly air or water for use in dentistry procedures, includes a structural unit for controllably heating a flowing medium disposed in a housing in a sealed manner such that an annular flow passage is formed between an interior wall of the housing and the structural unit. The structural unit includes a PTC resistor having end faces disposed between and in thermal and electrical contact with a pair of porous sintered metal heat exchanger elements at a non-zero angle to the direction of medium flow. Connectors on the opposing ends of the unit contact the sintered heat exchanger elements to flow connect the structural unit in a medium flow line and to electrically connect the PTC resistor to a heating control circuit. A flow passage extends from each connector into the respective sintered heat exchanger element so that the medium flows from one heat exchanger element to the other by flowing through the annular flow passage, thus providing a large heat exchange area in a small space.

28 Claims, 8 Drawing Sheets ns
DENTAL HANDPIECE FOR HEATING MEDIA UTILIZING A PTC RESISTOR AND SINTERED METAL COMPONENTS

TECHNICAL FIELD OF THE INVENTION

The invention relates to a device for controlled heating of media in a handpiece with a medium line that has associated with it an electric heating device for heating the medium that includes a PTC (Positive Temperature Coefficient) resistor and a heater circuit.

BACKGROUND OF THE INVENTION AND PRIOR ART

Handpiece of this kind having a heating device for heating media are known in particular in the case of dental spraying handpieces. The media used, such as water and air, must be heated to as constant a temperature as possible. However, this is very difficult to achieve in view of the different operating conditions. Disclosed in DE-OS 22 52 330 is a heating device with a through-flow heater in which the heating element is formed by a heating spiral. Heating spirals have the disadvantage that they require high heating power, are subjected to onerous demands on materials by the medium flowing by and cannot heat the media sufficiently uniformly. Furthermore, heating spirals cannot be used for continuous operation.

A device of the kind mentioned in the introduction is known from DE-OS 23 22 191. In this device a thermistor with a positive temperature coefficient, i.e. a barretter a low voltage, filament-type voltage regulator) of PTC-element, is used. In a comparatively complicated circuit the resistor operates as heater in the positive voltage half-wave and as sensor in the negative voltage half-wave, of which the output signal, together with the following circuitry, determines the current flow in the positive voltage half-wave. The double function of the thermistor has the disadvantage that there is only one voltage half-wave available for the heating phase so that the media are heated relatively slowly. Furthermore, there is the disadvantage that the control electronics are not separated from the heating device, so that maintenance of the heating devices is made difficult and exchange thereof is complicated.

A dental spraying handpiece is known from DE-OS 37 34 864 in which the electric heating devices, formed by means of heating spirals, form a detachable structural unit arranged in the handpiece.

OBJECT OF THE INVENTION

It is the object of the invention to provide a device of the kind mentioned in the introduction which allows a short heating-up period, simple maintenance of the heating device and determination of a particular upper temperature limiting value.

SUMMARY OF THE INVENTION

According to the invention there is provided a device for controlled heating of media in a handpiece having a medium line associated with which is an electric heating device for heating the medium and which includes a PTC resistor and a heater circuit, wherein said PTC resistor as heating element together with a heat exchanger forms a structural unit that lies in said heater circuit.

The advantages of the invention are substantially based on the fact that the structural unit, comprising PTC resistor and heat exchanger, enables the provision of a large exchange surface area in a very small space. The form of the heat exchanger is simple to manufacture and is connectable to the PTC resistor. A structural unit made in this way can easily be integrated into a dental handpiece as a heater. Since the structural unit has a small volume it enables the provision of a short heating-up period. As a purely passive element the structural unit facilitates connection of the medium lines and the heater circuit so that the structural unit as a heating element is easy to maintain and if necessary can be easily exchanged.

BRIEF DESCRIPTION OF THE DRAWINGS

Embodiments of the invention are shown by way of example with reference to the drawings and will be explained below.

The same reference numerals indicate the same elements.

DETAILED DESCRIPTION OF PREFERRED EMBODIMENTS OF THE INVENTION

Figure 2:
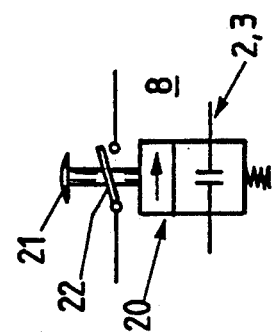
FIG. 2 shows a schematic representation of an electric, switch and a shut-off valve.

The dental spraying handpiece 1 shown comprises a gripping sleeve in which two medium lines 2, 3 are arranged that extend from a medium connection to a medium outlet where they are open to the surroundings.

One medium line is connected to a water supply (not shown), the other is connected to an air supply (not shown). Associated with the medium lines 2, 3 are respective electric heating devices 41, 42 with associated fluid flow heater devices 45, 46 for heating the media.

The electric heating devices 41, 42 have heater assemblies 71, 72 comprising PTC resistors 5 and heat exchangers 6, which form a structural unit and lie in the heater devices 45, 46 having circuit elements 8, 9, 10, of the electric heating device, 41, 42. The heater assemblies 71, 72 are built into a housing 4 that is inserted detachably in the gripping sleeve. The heater assemblies 71, 72 are in turn arranged detachably in the housing.

The medium lines 2, 3 are connected to the heater assemblies 71, 72 and the housings 4 so that the media can enter on one side of the heater assemblies 71, 72 and leave again on the other side in the medium lines 2, 3.

The housing 4 or the heater assemblies 71, 72 associated therewith each have two connections to which electric lines are connected. While the electric connection line 10 is led directly to the one connection 11 of each of the two heater assemblies 71, 72, the electric connection line 9 is led via a switch to the other electric connection 11 of the heater assembly 41, 42 (see FIG. 8). The heater assembly 71, 72 forms a structural unit.

The elements 8 represent the valves and switches for the electric lines and for the medium lines and are shown in more detail in FIG. 2. An electric switch 22 and a shut-off valve 20 for a medium line 2 or 3 can be actuated by a pushbutton 21. The shut-off valve can be formed as a pneumatic or magnetic valve. In the inoperative position the switch 22 is open and the shut-off valve 20 is in the blocking state. The flexible medium line 2, 3 is usually constricted from the outside so that medium cannot pass through. By actuating the pushbutton 21 the switch 22 is closed on the one hand, so that the heater assemblies 71, 72 begin to function. At the time the shut-off valve 20 is opened so that the media can travel through the handpiece to the medium outlet. The medium passages to the medium outlet can obviously also be separate. Both separate control for each medium and mixed control, for example when water is to be sprayed, are possible.

Figure 3:
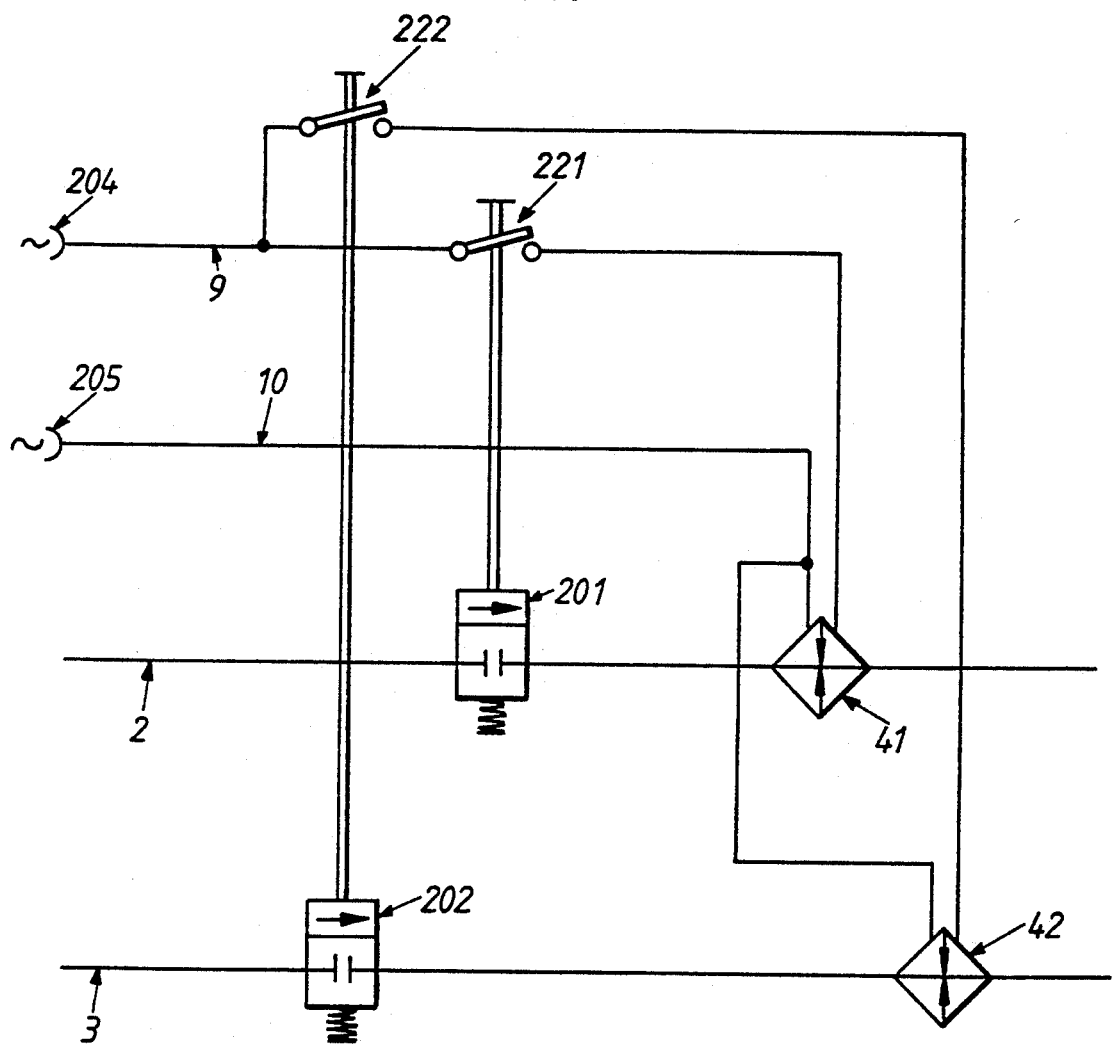
FIG. 3 shows a schematic representation of the heater circuit for the arrangement of FIG. 1.

FIG. 3 shows the electric control of the heating devices 41, 42 for the medium lines 2, 3. The energy supply and the medium supply for the heating devices 41, 42 is controlled by two arrangements, as shown in FIG. 2, each with an electric switch 221, 222 and each with a shut-off valve 201, 202. The switches 221, 222 are each connected to one of the heating devices 41, 42 and on the other side each to an electric connection line 9 that is connected to a voltage source via a terminal 204. The electric heating devices 41, 42 are each connected on the other side via the connection line 10 to a terminal 205 which lies on another pole of the supply voltage. The supply voltage and the control voltage for the heating devices 41, 42 thus lies between the two terminals 204, 205. An alternating voltage source of 24V effective voltage usually serves as voltage source.

Figure 4:
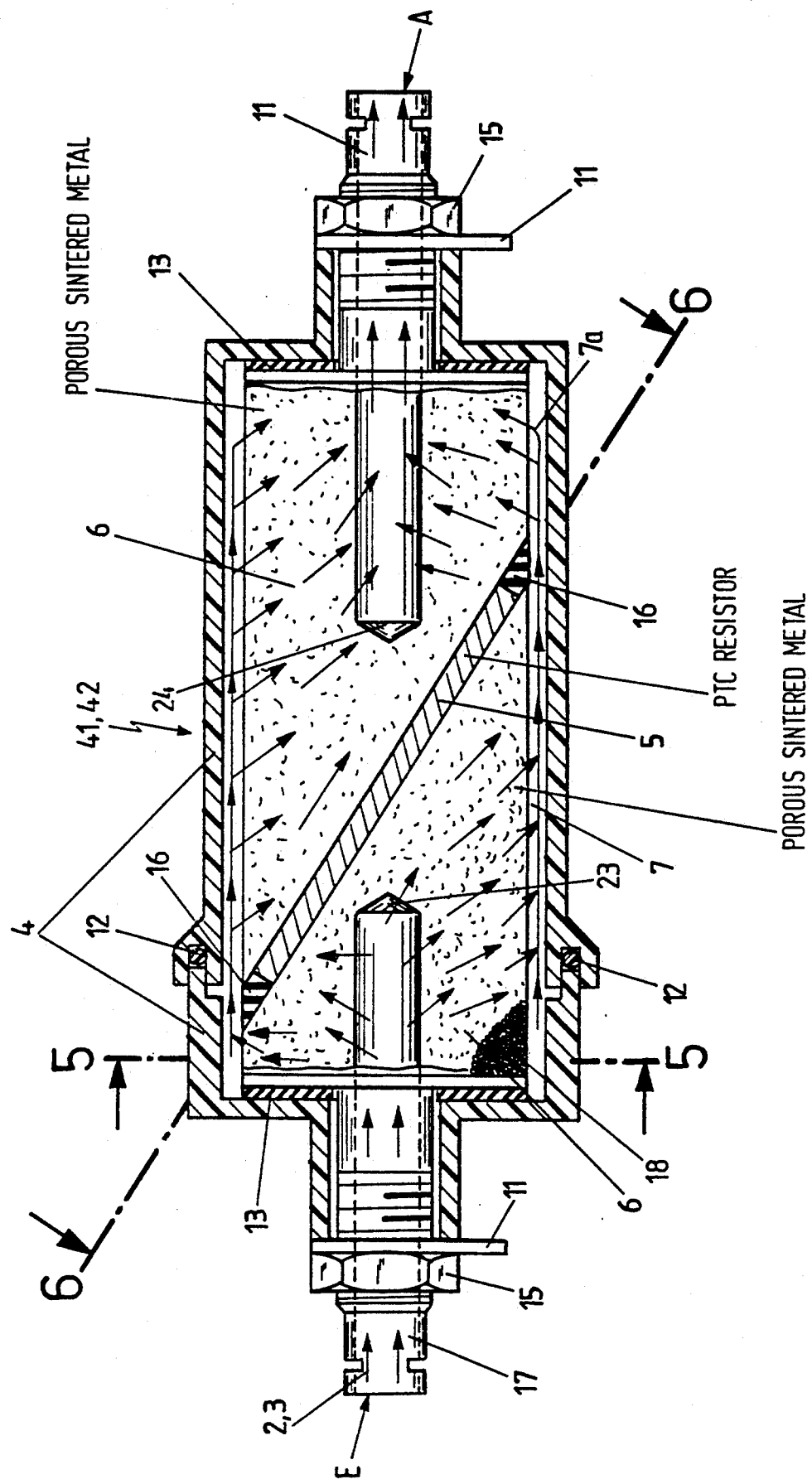
FIG. 4 shows a schematic representation of the PTC resistor with heat exchanger according to the invention.

A structural unit or heater assembly 71, 72 is shown, with the corresponding housing, to an enlarged scale in FIG. 4. The medium lines 2, 3 are connected to the medium inlet E and the medium outlet A preferably by socket nipple connections 17. The heater assembly 71, 72 is in a housing 4 that is made of an insulating or plastics material and is closed off from the outside in a medium-tight manner by a seal, preferably an 0-ring seal 12. Both the structural unit and the housing are cylindrical. On the end faces of the housing 4 there are connections 11 that are affixed to the housing or to the structural unit by a fastening nut 15 such that they are connected to the structural unit in an electrically conductive manner. A medium passage 7 is formed between the outer surface of the structural unit 5, 6 and the inner surface of the housing 4. At the ends the structural unit is connected against the housing 4 by a sealing rubber 13, so that it is medium-tight. The structural unit or the heater assembly 71, 72 itself comprises a barretter resistor or a PTC resistor 5 and a heat exchanger 6. The PTC resistor 5 is formed as a heating plate and affixed to both elements 6 in an electrically and thermally conductive manner. The PTC resistor serves as the actual heating element which, because of its positive temperature coefficient, assumes a state of equilibrium between the electric power taken up and a corresponding temperature. This state of equilibrium is assumed having regard on the one hand to the PTC resistor itself and on the other hand to the loss of heat to the surroundings. Loss of heat to the surroundings results in a reduction of temperature so that the resistance value falls and more electric power can be taken up. A new state of equilibrium is attained by self-regulation.

The heat exchanger 6 shown in FIG. 4 comprises two heat exchanger portions between which the PTC resistor 5 is arranged. The heat exchanger uses sintered metal parts that are not only made lumpy in the sintering process but also have a particular porosity. Depending on the degree of porosity the sintered heat exchanger elements can therefore be adapted to the predetermined media.

The medium supply and removal occur via holes 18 (not shown in detail) that are connected directly with the medium lines. The PTC resistor 5 has its extensive plate area inclined towards the cylinder axis of the heater assembly 71, 72. Towards the medium passage 7 the PTC resistor is insulated by an insulator 16. The PTC resistor 5 and the radially adjoining insulation form a barrier for the media. A medium flowing through the medium entrance E is therefore forced to penetrate the sintered material via the hole 23 adjoining the medium line 2, 3 and to flow from there to the medium passage 7. Behind the barrier formed by the PTC resistor 5 and the associated insulating material 16 the medium must then flow again via the sintered material and the hole 24 therein to the medium outlet A. This forced flow-through is made possible by the outer housing 4 that is sealed against the heater assembly 71, 72 at the structurally provided points. For easier maintenance the housing 4 is divided and the heating element 5, 6 is arranged detachably in the housing. The design of the heat exchanger with sintered metals enables a large heat exchanging surface in the smallest space. Furthermore the sintering process offers a heat exchanger form that is easy to manufacture. Overall, such a compact arrangement can be obtained that the heater assembly 71, 72 with housing 4 can also be integrated in duplicate in a dental handpiece. Owing to the large surface area the heater assembly 71, 72 enables a short heating-up period and, due to the fact that the media must flow via the medium passage 7 and through the sintered material 6 itself, it is provided that the temperature gradient of the medium remains small. The structural configuration of the heater assembly 71, 72 with housing makes easy connection of both the mediums and the electrical supply possible and thus, in the case of maintenance, enables easy access and simple exchange of the elements.

Furthermore, the compact construction of the heating element makes it possible that for dental use only one handpiece need be prepared, which can later be equipped or re-equipped with both the heater assemblies 71, 72 and the associated electrical circuitry, without problems.

Figure 5:
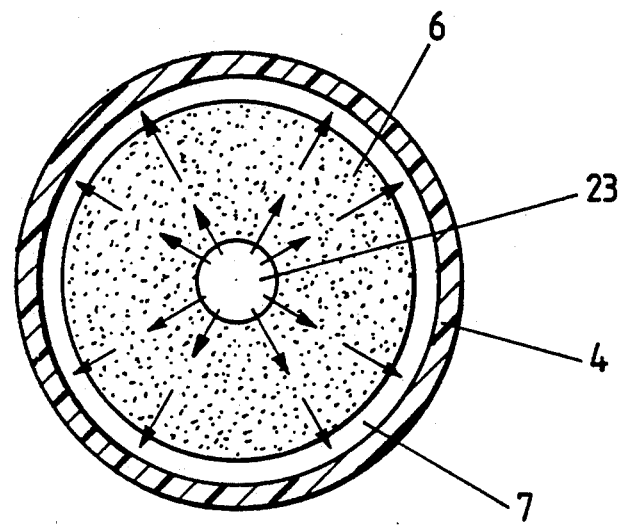
FIG. 5 and FIG. 6 show cross-sections through the structural unit shown in FIG. 4.
Figure 6:
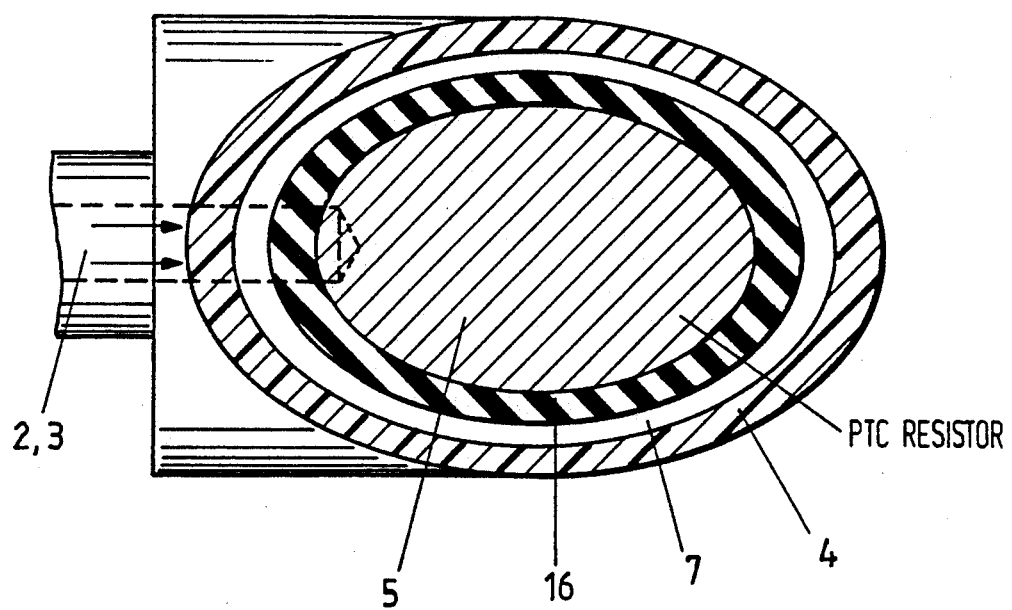

FIGS. 5 and 6 represent sections through the arrangement shown in FIG. 4 with reference to the sectional lines 5—5 and 6—6. From the Figures the principle of medium flow from the medium line through the heat exchanger 6 will once more become clear as will the structural configuration.

Figure 7A:
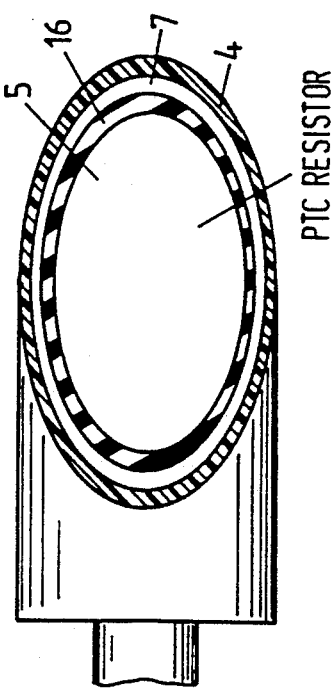
FIG. 7a shows a cross-sectional view of the unit shown in FIG. 4 having an ellipsoidal PTC resistor.
Figure 7B:
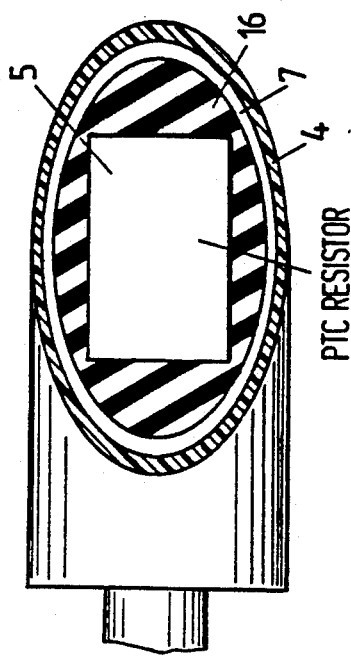
FIG. 7b shows a cross-sectional view of the unit shown in FIG. 4 having a rectangular PTC resistor.
Figure 7C:
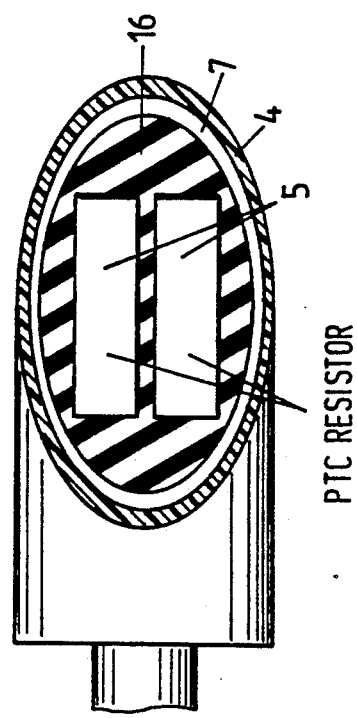
FIG. 7c shows a cross-sectional view of the unit shown in FIG. 4 having two rectangular PTC resistors.
Figure 7D:
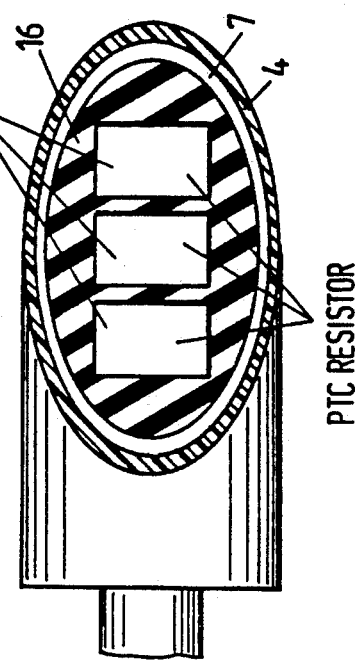
FIG. 7d shows a cross-sectional view of the unit shown in FIG. 4 having three rectangular PTC resistors.

FIG. 7a–7d show a few forms for the geometric shaping of the PTC resistors 5. In FIG. 7a) the PTC resistor has an ellipsoidal contour corresponding to the section through the substantially cylindrical shaped heater assembly 71, 72, in FIG. 7b) a rectangular cross-section. In FIG. 7c) two rectangular PTC resistors are arranged side by side and in FIG. 7d) three semi-conductor elements, rectangular in contour, are arranged side by side.

Figure 1:
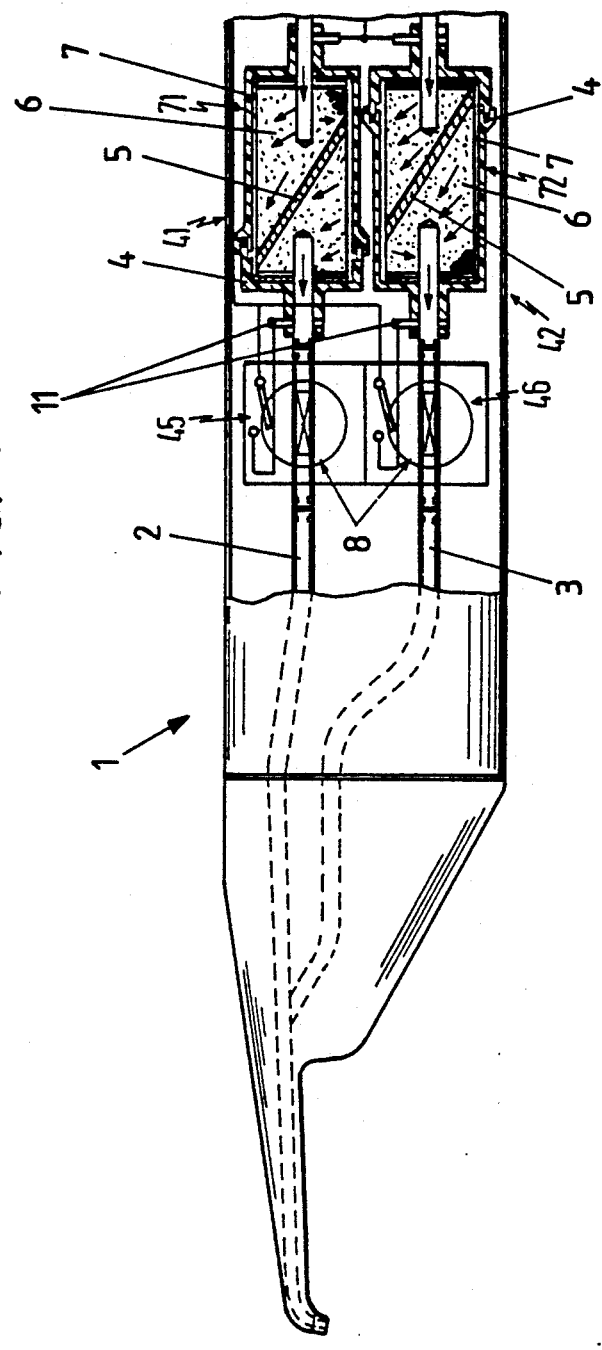
FIG. 1 shows a first exemplary embodiment of a device according to the invention in a handpiece.
Figure 8:
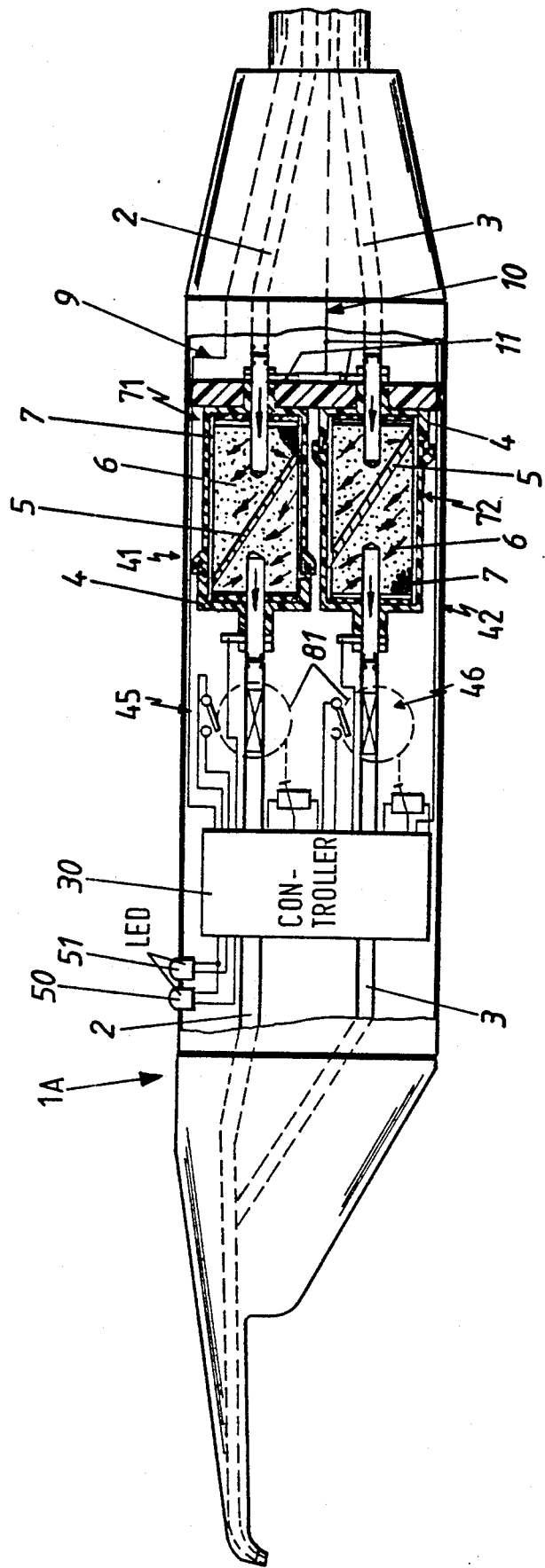
FIG. 8 shows a second exemplary embodiment of the device according to the invention in a handpiece.

FIG. 8 shows a second exemplary embodiment of the device 7a according to the invention. The heater assembly 71, 72 comprising the elements 5, 6 and the associated housing 4 are the same as those in FIGS. 1 and 4. The difference from the exemplary embodiment shown in FIG. 1 is the configuration of the heater fluid flow devices 45, 46 in which the heater assembly 71, 72 lies. Therefore only the differences with regard to FIG. 1 will be described below. The arrangement 8 shown in FIG. 1 is modified by an arrangement 81 in connection with the elements 30, 50 and 51. The switch and valve arrangement 81 is connected to an electronic controller 30. Connected to the electronic controller 30 are light emitting diodes 50, 51 which indicate a heating operation of the heating device 41, 42. The switch and valve arrangement 81 is shown more clearly in FIG. 9. With a pushbutton 31 an electric switch 32 can be closed which closes a circuit (to be described below) for the control of a controllable switching element. An variable resistor 33, which may be arranged in series with a variable resistor 34 provided if necessary, stands in operative connection with the pushbutton 31. The valve 20 for the medium lines 2, 3 is actuated by the pushbutton 31 simultaneously with the electric switch 32.

Figure 10:
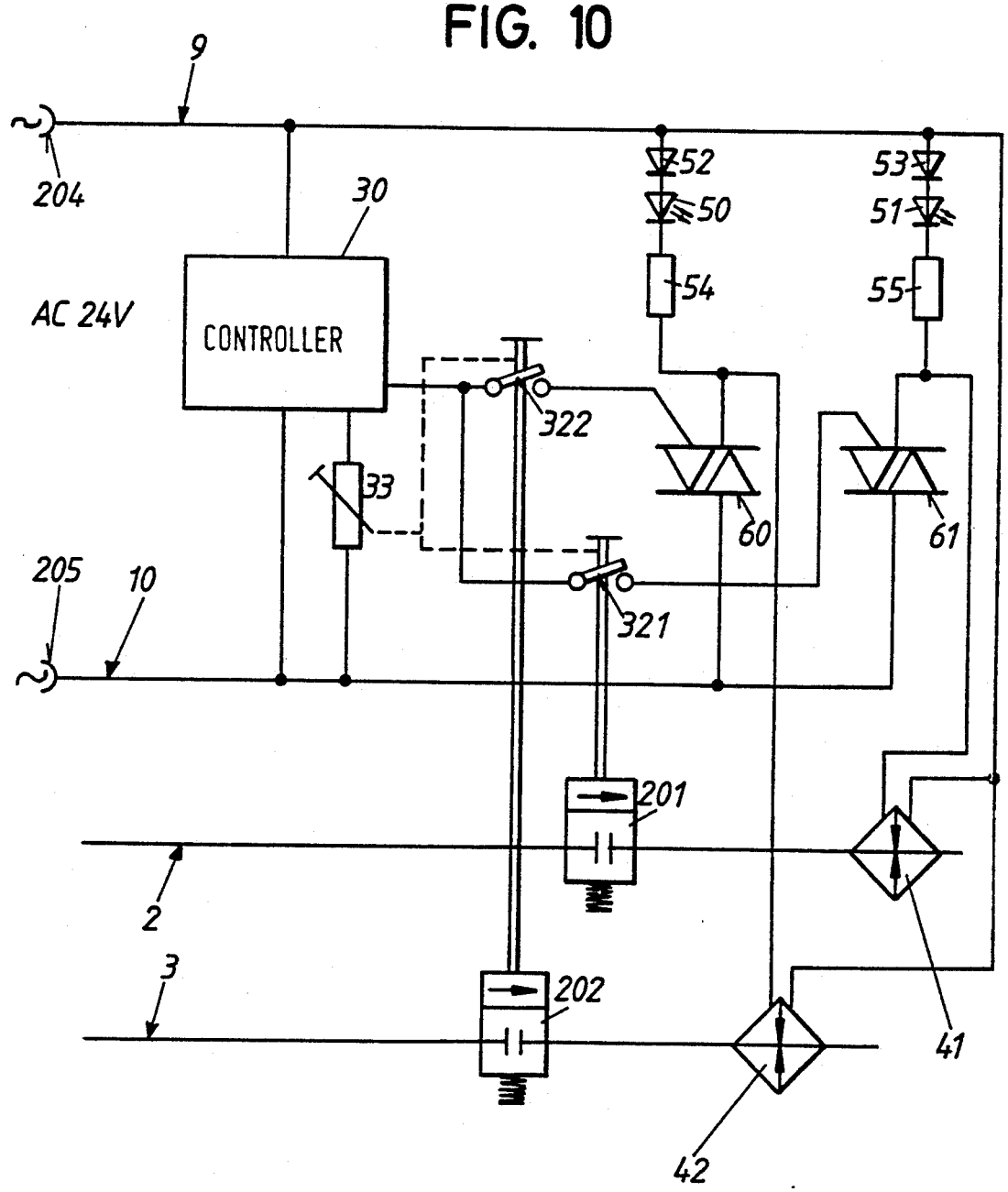
FIG. 10 shows a schematic electrical circuit diagram for the heater circuit for the device shown in FIG. 8, FIG. 11 and FIG. 12 show diagrams for explaining the controllable heating power for the arrangement shown in FIG. 8.

Details of the control are shown in FIG. 10. The valves 201 and 202 for the water medium passage 2 and the air medium passage 3 respectively are actuated by the switches 321 and 322. The two switches together with the controller 30 and the variable resistor 33 form a control element for the two controllable switching elements 60 and 61. The controllable switching elements are formed by triacs in this exemplary embodiment. The switches 321 and 322 control respective control electrodes of the triacs 60 and 61. In their load circuit the two triacs 60, 61 are connected on the one side via the line 10 to the supply voltage terminal 205. The other load-side connection of each of the two triacs 60, 61 is connected to an electric connection of the corresponding heating devices 42, 41. This load-output connection of each triac 60, 61 is further connected via a respective series circuit to the connection line 9. Each series circuit includes a diode 52, 53, a photodiode 50, 51 and a resistor 54, 55. This circuit serves to indicate when the triac 60, 61 is switched through, or the heating condition for the heating device 41, 42. The other electric connections of the heating devices 41, 42 are connected to the line 9 that is connected via the terminal 204 to the other pole of the supply voltage source.

Inserted between the lines 9 and 10 is the controller 30 of the control element and between the controller 30 and the line 10, is the variable resistor 33.

While the switch 321, 322 is responsible on the one hand for the medium control via the valves 201, 202 and on the other hand for the control of the triac 60, 61, the variable resistor 33 serves to set the desired heating power. In principle the heating power can be adjusted by a method known per se, for example by phase control.

Figure 11:
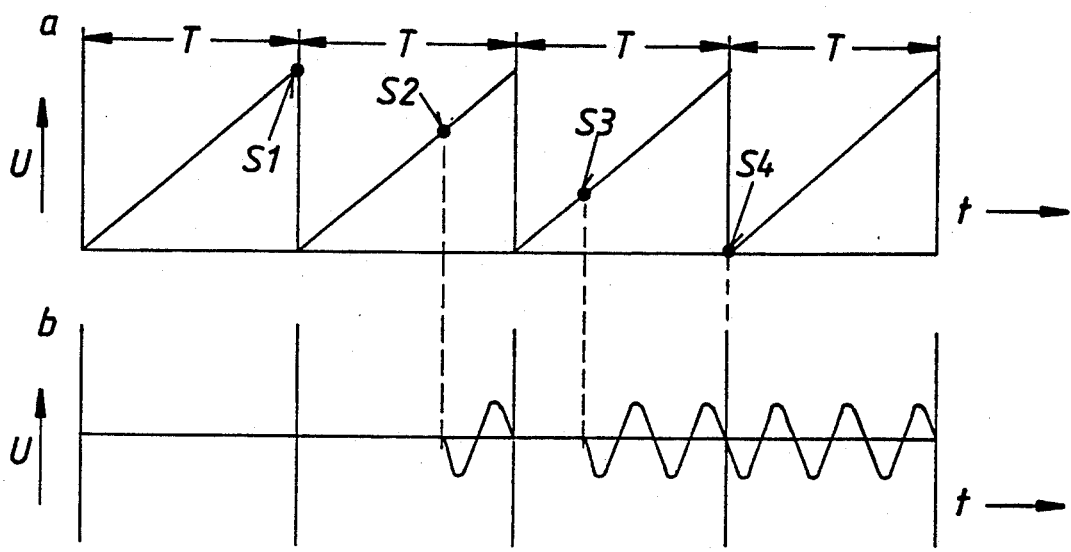

The controller 30 in this exemplary embodiment is formed as a multi-cycle control. For this purpose the controller 30, with the aid of a ramp generator, produces a ramp signal voltage which within each of its periods T rises linearly from 0 to a particular end value. Located on the pushbuttons and switches 321, 322 is the variable resistor 33 which changes its resistance value according to the actuator travel or actuating force of the pushbutton. The resistance value in turn determines the threshold at which the controller 30 switches through the signal at the line 9 to the switch 321, 322 and to the control connection of the thyristor 60, 61. This is shown by way of example with reference to FIG. 11 by the different switching points S1 to S4.

In dependence upon the resistance value of the trimmer 33 the controller 30 therefore controls the triacs 60, 61 to turn on (pass current through) at different moments in the respective ramp function so that, before the triac is switched off by the falling edge of the ramp generator voltage, only a particular number of multi-cycle signals can reach the triac 60, 61 and the heating device 41, 42. This is demonstrated with reference to FIG. 11b). Distinctions are made between switched off heating, an intermediate heating range and maximum heating power. In principle the heating power can thus be set between 0 and 100%. In this way adaptation of the electric power to medium consumption is achieved. It is obviously also possible, in contrast to FIG. 10, to adjust the heating powers for the heating devices 41, 42 separately for which purpose either the electronics must be designed accordingly or two variable resistors 33 must be provided.

Figure 9:
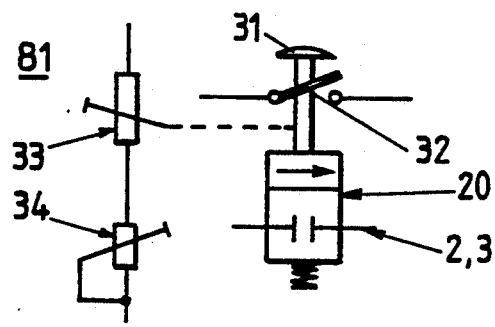
FIG. 9 shows a schematic representation for the medium and heating control.
Figure 12:
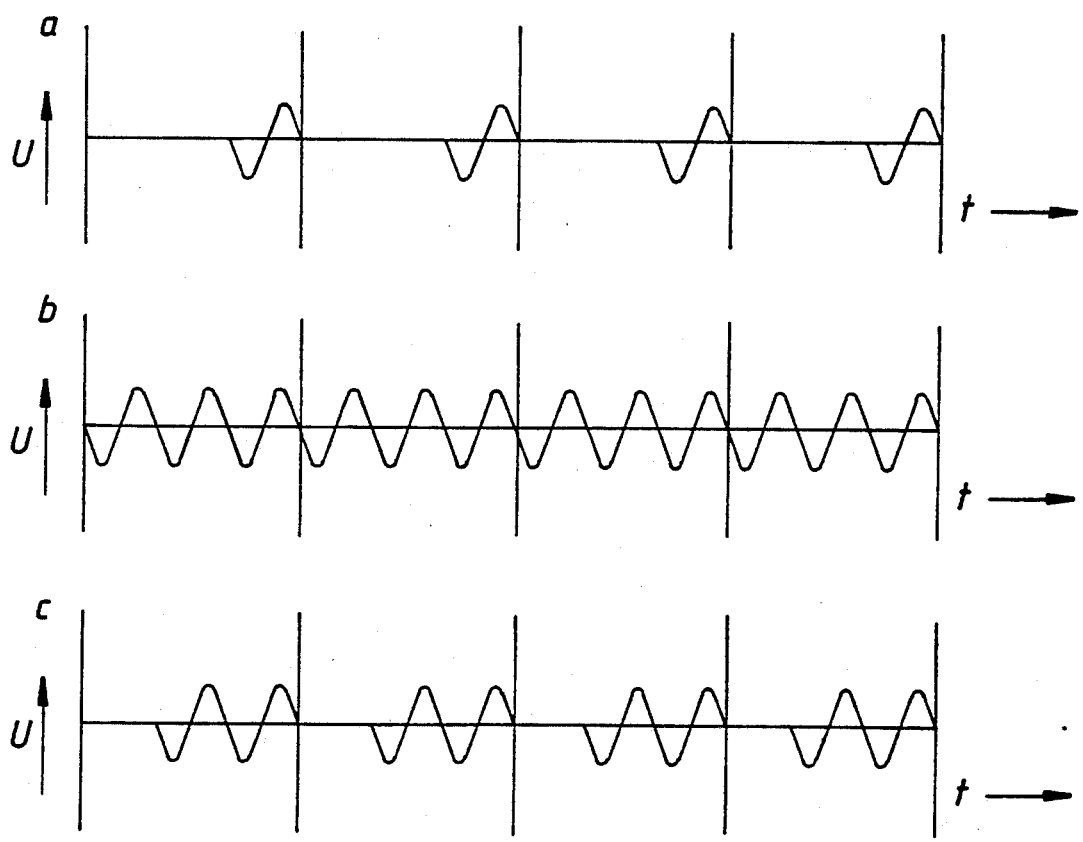

In another embodiment adjustment of the heating power occurs via an external potentiometer 34 shown in FIG. 9, that can be adjusted separately to a fixed heating power by the user. The heating power is thus independent of the amount of medium through-flow or the actuator travel or the actuating force of the trimmer 33 or the pushbuttons 321, 322. This operating condition is shown with reference to FIG. 12 in which the conditions a) for minimum heating power, b) for maximum heating power and c) for a limit to the heating power by way of a variable adjustable external potentiometer, are shown.

What is claimed is:

1. A dental handpiece for heating a medium, comprising:
   a medium line, disposed in a longitudinal direction, which transports the medium;
   a heating control circuit which controls the heating of the medium;
   a housing, having an interior and an exterior, coupled to the medium line and having holes which form passages from the interior of the housing to the exterior of the housing;
   a structural unit mounted within the housing in a sealed manner which controllably heats the medium flowing through the medium line, wherein the structural unit has opposing ends pointing in the longitudinal direction of the medium line and includes a PTC resistor disposed in electrical and thermal contact with a heat exchanger which is formed of an electrically conductive material; and
   connectors located on the opposing ends of the structural unit which penetrate the holes of the housing to connect the structural unit to the medium line, wherein at least one of the connectors includes an electrical connector disposed between the housing and a portion of he medium line adjacent to the housing which electrically connects the PTC resistor to the heating control circuit.

2. A device according to claim 1, wherein said PTC resistor is in the form of a plate.

3. A device according to claim 1, wherein said structural unit has a substantially cylindrical form.

4. A device according to claim 3, wherein said PTC resistor is in the form of a plate and its plate-like area substantially forms a separating plane in the cylindrical form and is inclined towards the cylinder axis.

5. A device according to claim 3, wherein the PTC resistor is in the form of a plate and the plate-like area of the PTC resistor corresponds substantially to the cross-sectional area through the cylindrical form.

6. A device according to claim 1, wherein a plurality of PTC resistors arranged side by side are provided.

7. A device according to claim 1, wherein said structural unit is arranged detachably in said housing.

8. A device according to claim 7, wherein said structural unit and said housing form a medium passage, wherein upon entering said structural unit the medium flows through one element of said heat exchanger, then flows through another element of said heat exchanger after flowing through said medium passage.

9. A device according to claim 8, wherein said medium passage extends between the outer periphery of said structural unit and the inner periphery of said housing, which is substantially cylindrical, and wherein the associated end faces are sealed from one another.

10. A device according to claim 1 wherein said heater circuit includes a controllable switching element that can be actuated by a control element.

11. A device according to claim 10, wherein said controllable switching element includes a triac or a thyristor.

12. A device according to claim 10, wherein a shut-off valve for said medium line is coupled to said control element.

13. A device according to claim 10, in said control element includes a control device that can be activated by a switch and which controls the controllable switching element.

14. A device according to claim 13, wherein said control device issues signals with which the heating power of the PTC resistor can be adjusted.

15. A device according to claim 13, wherein said control device sends out multi-cycle signals, the duration of which can be set by a trimmer element.

16. A device according to claim 15 wherein said trimmer element can be adjusted by said control element.

17. A device according to claim 1, wherein a heating operation is indicated optically.

18. A device according to claim 1, wherein said structural unit with said housing is arranged detachably in said handpiece.

19. The dental handpiece of claim 1, wherein the housing is transversely divided and comprises first and second housing portions which are sealed from one another by a ring seal.

20. The dental handpiece of claim 1, wherein the heat exchanger is made of sintered metal.

21. The dental handpiece of claim 20, further including a passage between each of the connectors and an inside of the heat exchanger.

22. The dental handpiece of claim 1, wherein the housing and the structural unit have cross-sectional dimensions which are larger than the cross-sectional dimensions of the medium line and wherein the housing is box-shaped, having longitudinal and transverse walls.

23. The dental handpiece of claim 22, further including seals disposed between the transverse walls of the housing and the opposing ends of the structural unit.

24. A dental handpiece for heating a medium flowing through a medium line disposed in a longitudinal direction and having an axis in the direction of flow of the medium, comprising:
   a heating control circuit which controls the heating of the medium;
   a housing, having an interior and an exterior, coupled to the medium line having holes which form passages from the interior of the housing to the exterior of the housing;
   a structural unit which controllably heats the medium flowing through the medium line, wherein the structural unit includes two heat exchanger elements formed of sintered metal and a PTC resistor which is electrically connected to the heating control circuit and has end faces disposed between the two heat exchanger elements at a non-zero angle to the medium flow axis and wherein the structural unit has opposing ends pointing in the longitudinal direction of the medium line and is disposed within the housing in a sealed manner such that a ring-shaped medium flow passage is formed between an interior wall of the housing and the structural unit;
   connectors located on the opposing ends which penetrate the holes of the housing to connect the structural unit to the medium line; and
   a passage from each one of the connectors to an inside of the structural unit.

25. The dental handpiece of claim 24, wherein the structural unit and the housing have cross-sectional dimensions which are larger than the cross-sectional dimensions of the medium line and wherein the housing is box-shaped, having longitudinal and transverse walls.

26. The dental handpiece of claim 25, further including ring seals disposed between the transverse walls of the housing and the opposing ends of the structural unit.

27. A dental handpiece for heating a medium, comprising:
   a medium line, disposed in a longitudinal direction, which transports the medium;
   a heating control circuit which controls the heating of the medium;
   a housing, having an interior and an exterior, coupled to the medium line, having holes which form passages from the interior of the housing to the exterior of the housing, wherein the housing is box-shaped, having longitudinal and transverse walls, and is transversely divided, including two housing portions which are sealed from one another by a ring seal;
   a structural unit mounted within the housing in a sealed manner, which controllably heats the medium flowing through the medium line, wherein the structural unit has opposing ends pointing in the longitudinal direction of the medium line and includes a PTC resistor, which is electrically connected to the heating control circuit, and a heat exchanger; and
   connectors, located on the opposing ends of the structural unit, which penetrate the holes of the housing to connect the structural unit to the medium line;
   wherein the structural unit and the housing have cross-sectional dimensions which are larger than the cross-sectional dimensions of the medium line.

28. The dental handpiece of claim 27, including further ring seals disposed between the transverse walls of the housing and the opposing ends of the structural unit.

* * * * *